United States Patent [19]

Kohler et al.

[11] Patent Number: 5,211,649

[45] Date of Patent: May 18, 1993

[54] VENOUS CUFF APPLICATOR, CARTRIDGE AND CUFF

[75] Inventors: Wolfgang W. Kohler, New South Wales, Australia; Paul Di Cesare, Norwalk, Conn.; Paul Mulhauser; Douglas Spranger, both of New York, N.Y.

[73] Assignee: Vaso Products Australia Pty. Limited, New South Wales, Australia

[21] Appl. No.: 279,702

[22] Filed: Dec. 12, 1988

[30] Foreign Application Priority Data

Feb. 10, 1987 [AU] Australia ................. PI0271
Apr. 16, 1987 [AU] Australia ................. PI1485
Oct. 12, 1987 [AU] Australia ................. PI4826

[51] Int. Cl.$^5$ ............................... A61B 17/00
[52] U.S. Cl. ........................... 606/139; 606/143; 606/153; 606/158
[58] Field of Search .............. 606/139-143, 606/151, 153, 155-158; 227/19, 67; 7/170; 29/235, 270, 278; 81/9.3

[56] References Cited

U.S. PATENT DOCUMENTS

| | | |
|---|---|---|
| 3,111,945 | 9/1984 | von Solbrig . |
| 3,254,680 | 6/1966 | Caveney et al. ............... 81/9.3 |
| 3,435,823 | 4/1969 | Edwards . |
| 3,687,138 | 8/1972 | Jarvik . |
| 3,892,241 | 7/1975 | Leveen .................... 606/158 |
| 4,050,465 | 9/1977 | Périssé ................... 606/139 |
| 4,349,028 | 9/1982 | Green ...................... 606/143 |
| 4,556,060 | 12/1985 | Perlin . |
| 4,592,355 | 6/1986 | Antebi .................. 606/157 X |
| 4,904,254 | 2/1990 | Lane ................... 606/153 X |

FOREIGN PATENT DOCUMENTS

| | | |
|---|---|---|
| 2206377 | 8/1978 | Australia . |
| 117981 | 9/1984 | European Pat. Off. . |
| 0286921 | 10/1988 | European Pat. Off. ........... 606/143 |
| 0406724 | 1/1991 | European Pat. Off. ........... 606/139 |
| 8202867 | 9/1982 | World Int. Prop. O. . |

Primary Examiner—Robert A. Hafer
Assistant Examiner—Brian F. Hanlon
Attorney, Agent, or Firm—Oblon, Spivak, McClelland, Maier & Neustadt

[57] ABSTRACT

An applicator for applying a strap around a vein at the site of a defective venous valve includes a handle portion and a removable cartridge. One end of the strap is anchored on the anvil of the cartridge and the free end is looped around the vein and passed through an opening in the cartridge to overlie the anchored end. The free end of the strap is connected to a strap puller within the cartridge which is coupled to a strap puller extension within the handle when the cartridge is inserted in the handle. The perimeter of the loop is adjusted by moving the tensioner on the handle. When the loop perimeter is at its desired value, the triggers on the handle are pressed to drive a staple through the overlying portion of the strap. A knife within the cartridge cuts the excess strap from the loop.

13 Claims, 14 Drawing Sheets

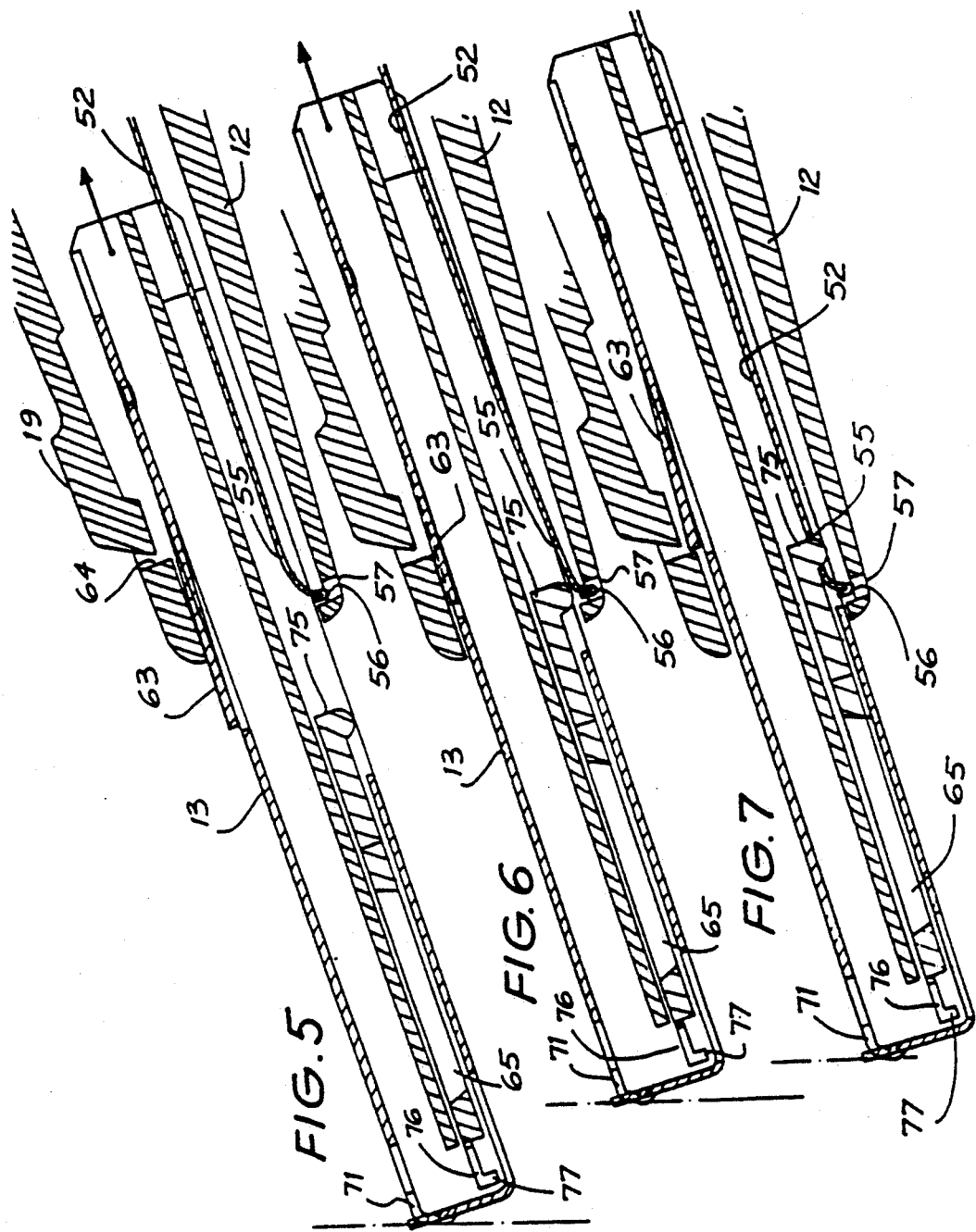

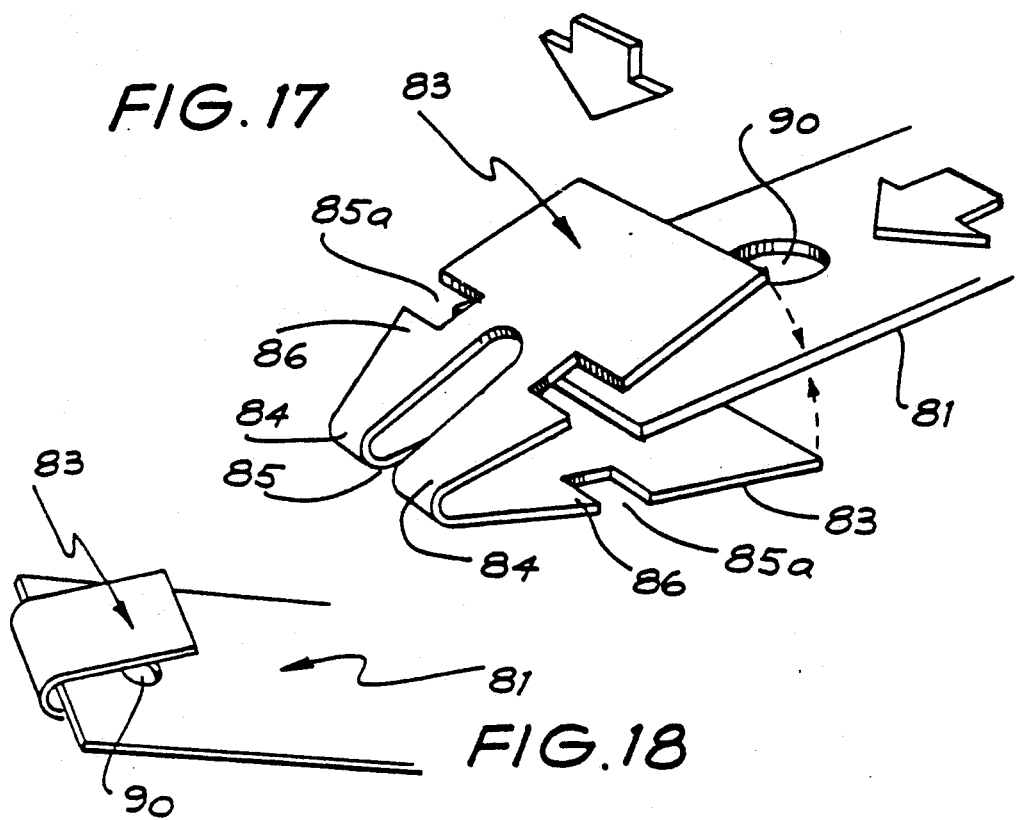
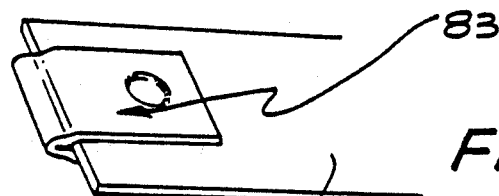
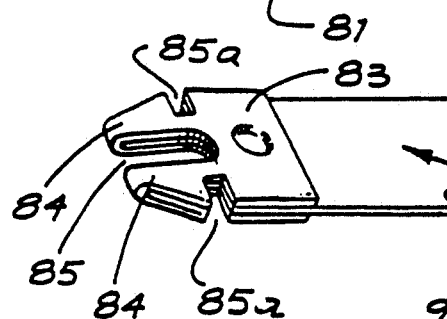
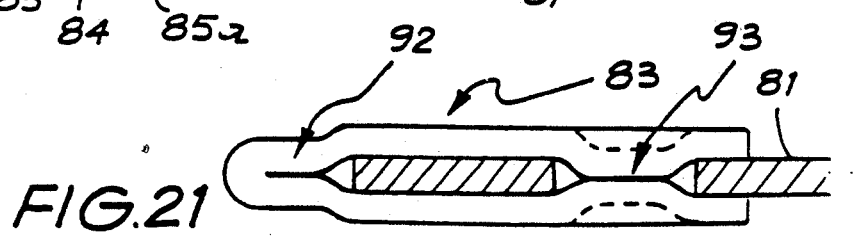

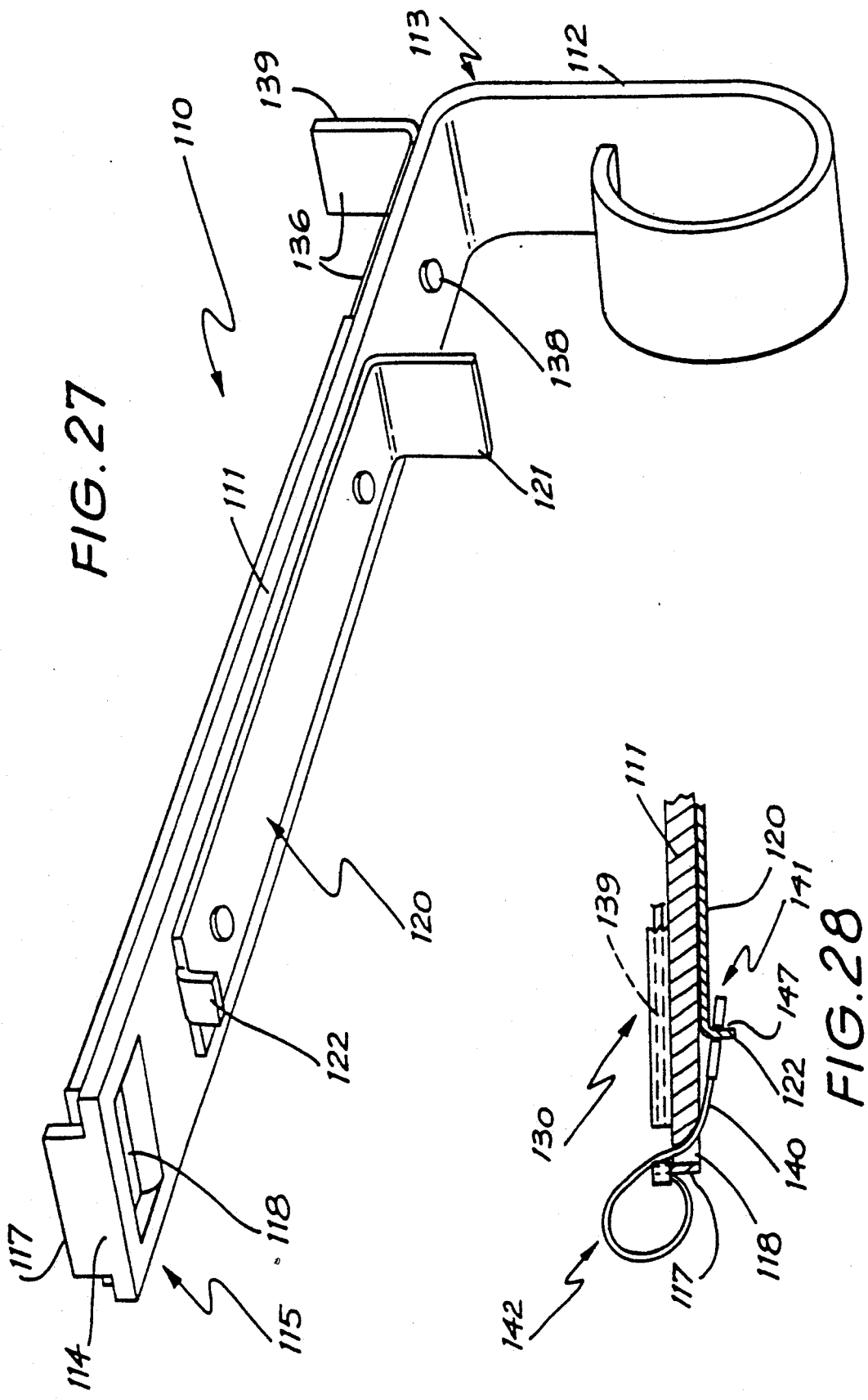

VENOUS CUFF APPLICATOR, CARTRIDGE AND CUFF

This is a continuation application of PCT/AU98/00036 filed Feb. 10, 1988, now abandoned.

TECHNICAL FIELD

This invention relates to apparatus for applying straps or cuffs around an object.

For the sake of convenience, the invention will be described in relation to the application of a cuff around a vein at the site of an incompetent venous valve but it is to be understood that the invention is not limited thereto as the applicator may be employed wherever it is desired to apply and secure a strap or cuff around an object.

BACKGROUND ART

International Patent specification PCT/AU87/00215 describes a cuff for restoring the competence of an incompetent venous valve. Venous valves initially fail because of dilatation of the vein wall in the region of the valve. As a consequence of the dilatation of the vein wall, the valve cusps do not seal against one another and thereby allow retrograde flow of blood.

According to the teaching of the abovementioned patent specification, a strap of bio-compatible, non-reactive material is encircled around the vein at the site of the valve and its circumference is reduced until the valve is competent again. When the desired circumference has been set, the overlapping ends of the strap are sutured together to form a cuff around the vein at the valve site. The free end of the strap may be removed.

It is an object of this invention to provide an applicator for applying a strap or cuff such as a venous cuff in order to simplify the method of applying the cuff and to minimize the time taken to apply the cuff.

It is a further object of the invention to provide an applicator for a venous cuff that permits a surgeon, working by himself, to apply the strap around the vein, adjust the diameter of the cuff, and fix the overlapping portions of the strap.

DISCLOSURE OF THE INVENTION

According to the invention there is provided an applicator for applying an elongated strap portion around an object, said applicator comprising means for anchoring one end of the strap, means movable with respect to the anchoring means adapted to engage the other end of the strap after it has been formed into a loop around the object and to move said other end of the strap so as to adjust the diameter of the cuff formed by the loop, and, means for securing the overlapping portions of the strap.

The means for securing the overlapping portions of the strap together may be one or more staples mounted within a stapling gun mounted on the body portion. When a stapling gun is used, the anvil against which the staple is closed may conveniently be formed on the means for receiving the strap.

In a preferred form of the invention, the staple is housed within a cartridge that contains the anvil against which the staple is closed. The cartridge may also contain a staple driver and a cuff adjustment puller or parts of those components.

The applicator may incorporate cutting means for trimming off any excess of the strap once the overlapping portions have been secured together. Automatic feeding means may be provided to feed the strap around the vein and back to the applicator so that the free end of the strap may be secured to the slidable engagement means on the body portion.

The applicator may incorporate a single strap and associated securing means or a plurality of straps and associated securing means. Alternatively, the applicator may not incorporate any straps (the straps being handled separately by the surgeon) but instead utilize a plurality of securing means so that the applicator may be readily used to apply a plurality of straps.

The applicator may be constructed as a disposable implement which is to be discarded once used for a single or multiple cuff application. On the other hand, the applicator may be constructed for ongoing use in which case regard must be had for the requirements of re-sterilization after each operation.

The overlapping portions of the strap may be secured together in any convenient way other than by staples as mentioned above. For example, an appropriate adhesive may be used and, in some circumstances, pressure or heat-based joining techniques may be employed. Mechanical or material coupling of the overlapping portions with each other may be used. Furthermore, a stud or the like may be carried by the end of the strap held captive of the body portion of the applicator and arrangement made to secure the overlapping portion of the strap to the stud.

According to another aspect of the invention there is provided a cartridge for the applicator referred to above. In one form of the invention, the cartridge consists of a housing which supports a stapler driver, an anvil, a staple adapted to be moved towards the anvil by the action of the staple driver and a cuff puller adapted to engage the leader of a cuff passed over the anvil. Preferably, the cartridge also contains a clamp for holding the cuff in position on the anvil.

In another form of the invention, the cartridge only contains the staple, the anvil and means for holding the cuff.

According to yet another object of the invention there is provided a cuff comprising a band of biocompatible implantable material, the band being of sufficient length to encompass a vessel with portions of the band overlapping, said band having a head portion adapted to be secured to an applicator and a leader portion adapted to be coupled to a cuff adjustor.

BRIEF DESCRIPTION OF THE DRAWINGS

In order that the invention may be more readily understood and put into practical effect, reference will now be made to the accompanying drawings in which:

FIG. 5 is an enlarged cross-sectional view of the cartridge end of the applicator shown in FIG. 1 with the cartridge being inserted, FIG. 6 is a view similar to FIG. 5 showing the manner in which the cuff adjustment puller of the cartridge engages the cuff puller extension of the applicator, FIG. 7 is a side elevational view similar to FIG. 6 showing engagement of the puller of the cartridge with the puller extension of the applicator, FIG. 17 is a view similar to FIG. 14 of a modified form of cuff leader, FIG. 18 is a view similar to FIG. 17 showing the first step of preparing a further modified form of cuff leader, FIG. 19 is a view similar to FIG. 18 showing the second step of preparation of the cuff leader, FIG. 20 is a view similar to FIG. 19 of the completed cuff leader, FIG. 21 is a cross-sectional view of the cuff shown in FIGS. 17 and 20.

FIG. 27 is a perspective view, from below, of the applicator shown in FIG. 26, FIG. 28 is a partially cut away, cross-sectional side elevational view of the cuff holding end of the applicator shown in FIGS. 26 and 27.

BEST MODES FOR CARRYING OUT THE INVENTION

Figure 1:
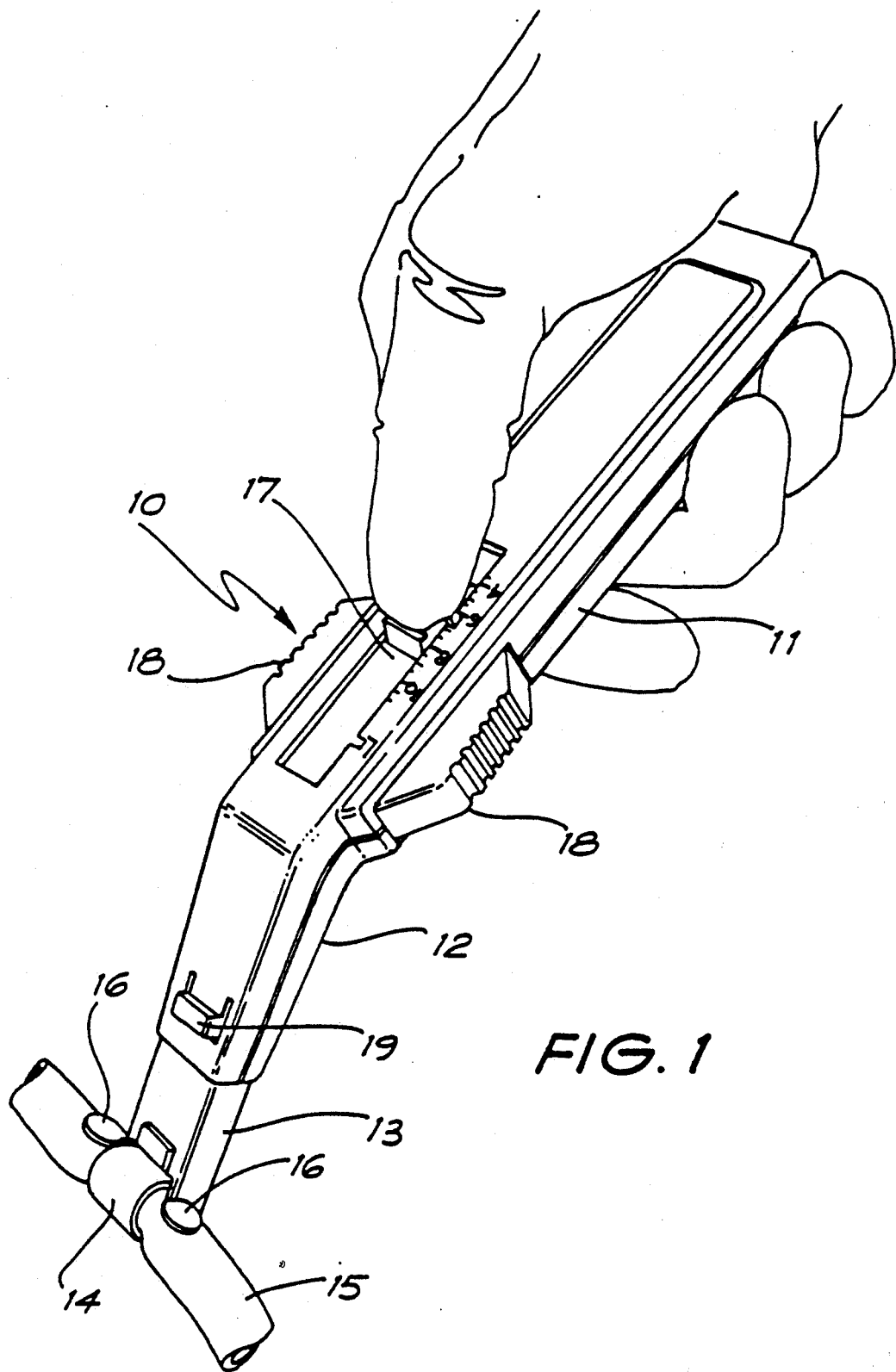
FIG. 1 is a perspective view of an applicator according to one embodiment of the invention.

The applicator 10 shown in FIGS. 1 to 4 includes a body portion 11 adapted to be held by hand and a cartridge-receiving portion 12 which supports a replaceable cartridge 13. The applicator 10 is suitable for applying a venous cuff 14 around a vein 15. When in position, the cuff 14 is secured to surrounding tissue by tabs 16.

In this instance, the cartridge 13 includes a staple, and staple anvil (as will be described below) and supports the cuff 14. The cuff 14 is manipulated by a tensioner 17 to adjust the diameter of the cuff 14 and the staple is dispensed from the cartridge 13 to secure the overlapping portions of the cuff together by the action of opposed side actuators or trigger means 18. The cartridge 13 is ejected from the applicator 10 by the action of the eject button 19.

Figure 3:
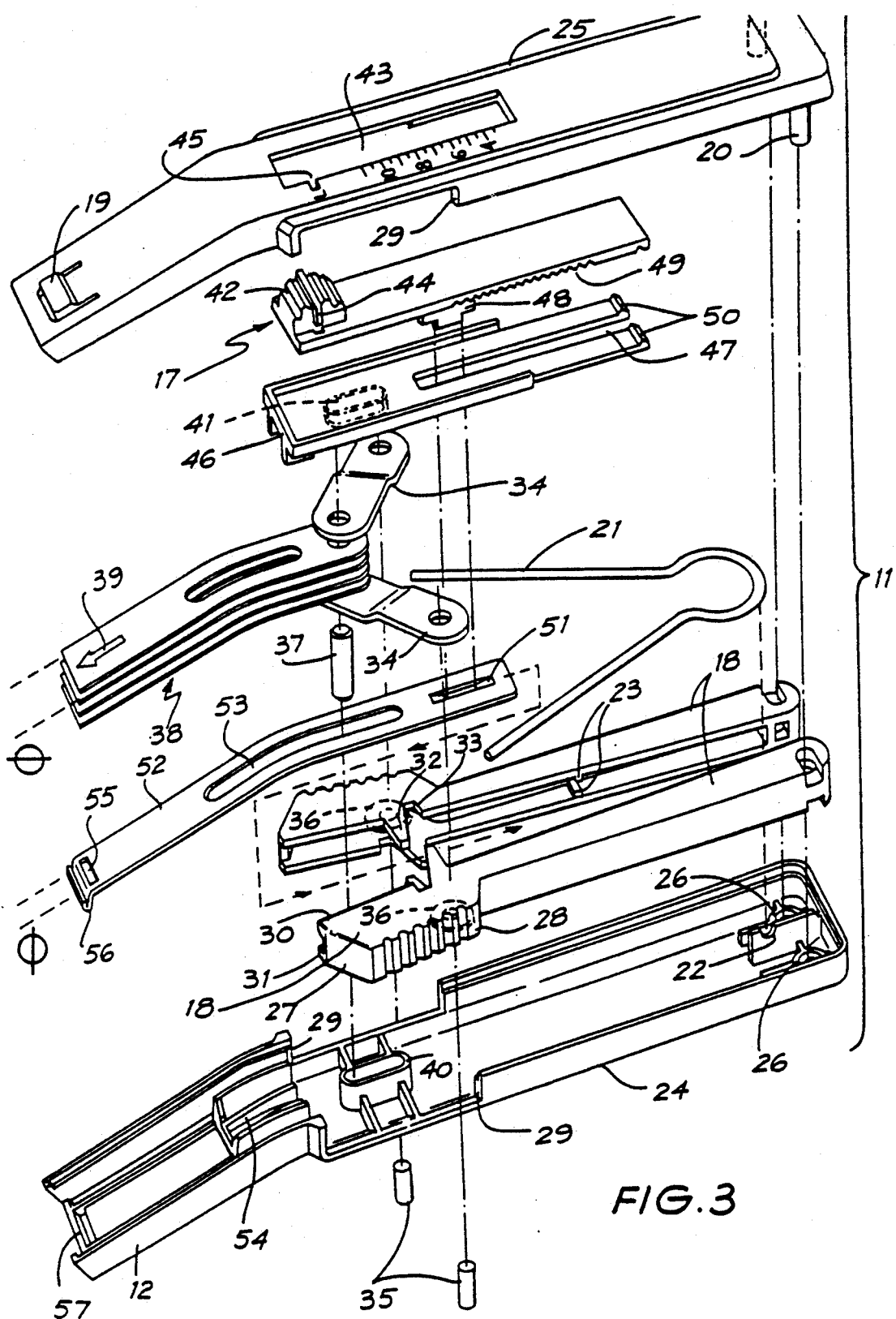
FIG. 3 is an exploded view of the body portion of the applicator shown in FIGS. 1 and 2.

As indicated in FIG. 3, the side actuators or triggers 18 are pivoted on the base 24 of the body portion 11 about pins 20 which extend downwardly from the rear end of cover 25 of the body portion 11 and engage in recesses 26 at the rear of the base 24. The enlarged front end 27 of each actuator or trigger 18 has an engagement face 28 which projects outwardly through respective apertures 29 in the base 24.

The enlarged front end 27 of each trigger 28 is partly defined by top face 30 and bottom face 31 each of which have a mating projection 32 and a recess 33 for limiting the inward movement of the triggers 18. Toggle links 34 are pivoted to the front end 27 of each trigger 18 about pins 35 which are retained in bases 36. The toggle links 34 are joined by link pin 37 to a staple driver extension 38. The pin 37 slides in elongated recess 40 formed on base 24 and an upper recess 41. When the side actuators or triggers 18 are pressed inwardly, the toggle links 34 force the staple driver extension 38 in the direction of arrow 39. When the side actuator triggers 18 are released, the spring 21 forces the actuators or triggers 18 outwardly which in turn move the staple driver extension 38 in the opposite direction to arrow 39.

The tensioner 17 has a thumb slide abutment 42 which slides in recess 43 formed in the cover 25 of body portion 11. The abutment 42 has a transverse lug 44 which can engage in recess 45 in the side of tension recess 43 to lock the tensioner 17 in the load position L. The tensioner 17 slides along a support bed 46 which has an elongated slot 47 that receives the drive lug 48 of the tensioner 17. Incremental movement of the tensioner 17 is achieved by means of serrations 49 in the bottom face of the tensioner 17 which engages, in turn, the resilient ends 50 of the support bed 46.

The drive lug 48 of the tensioner 17 is engaged in aperture 51 of cuff puller extension 52. The cuff puller extension 52 has an elongated slot 53 to permit the cuff puller extension 52 to slide clear of the link pin 37. The front of the puller extension 52 is supported by a housing 54 on the base 24. At the end of the puller extension 52 there is a slot 55 and a downwardly depending lug 56 which can be deflected downwardly into the recess 57 formed in the base 24.

Figure 2:
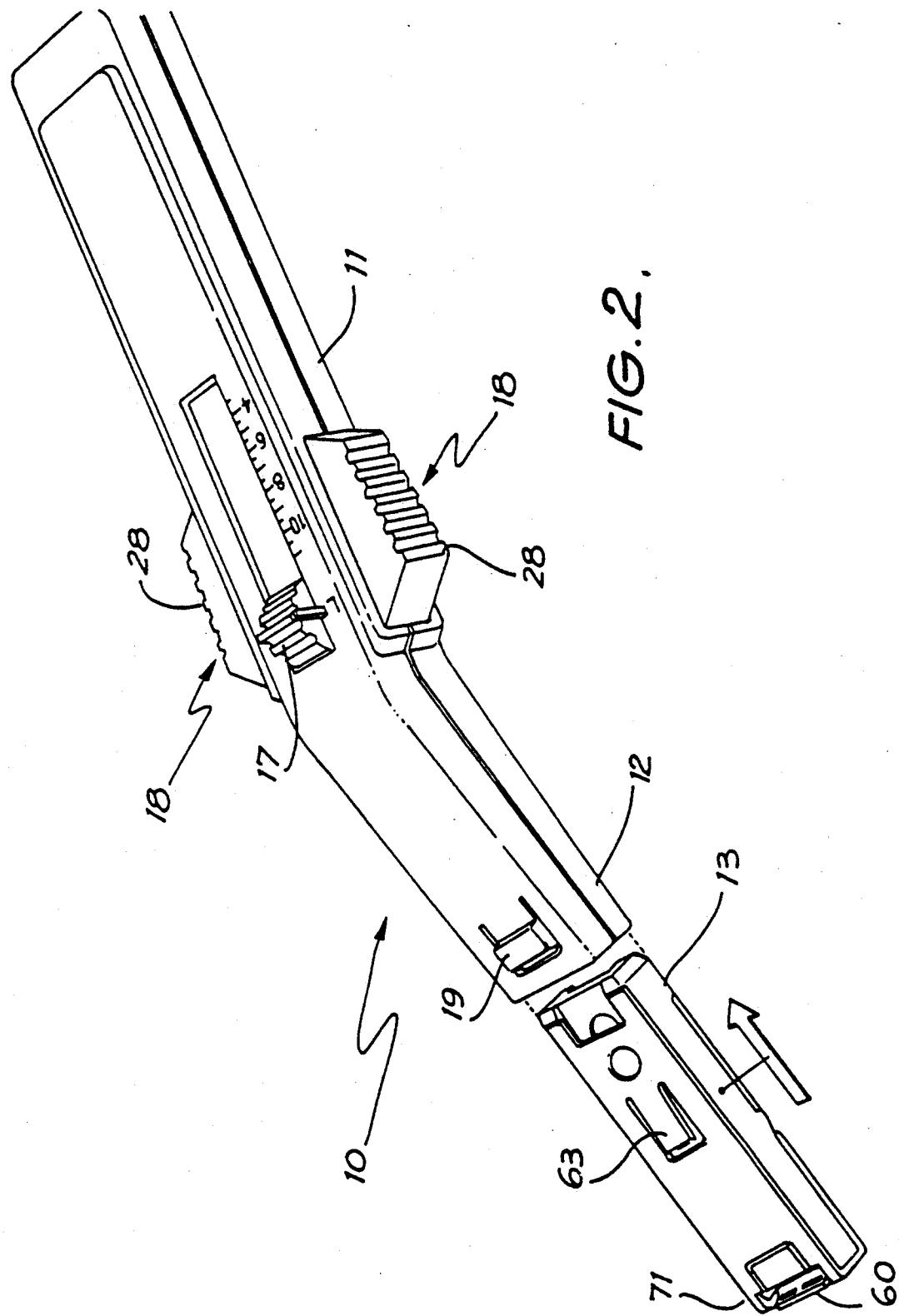
FIG. 2 is a perspective view of the cartridge being attached to the body portion of the applicator shown in FIG. 1.
Figure 4:
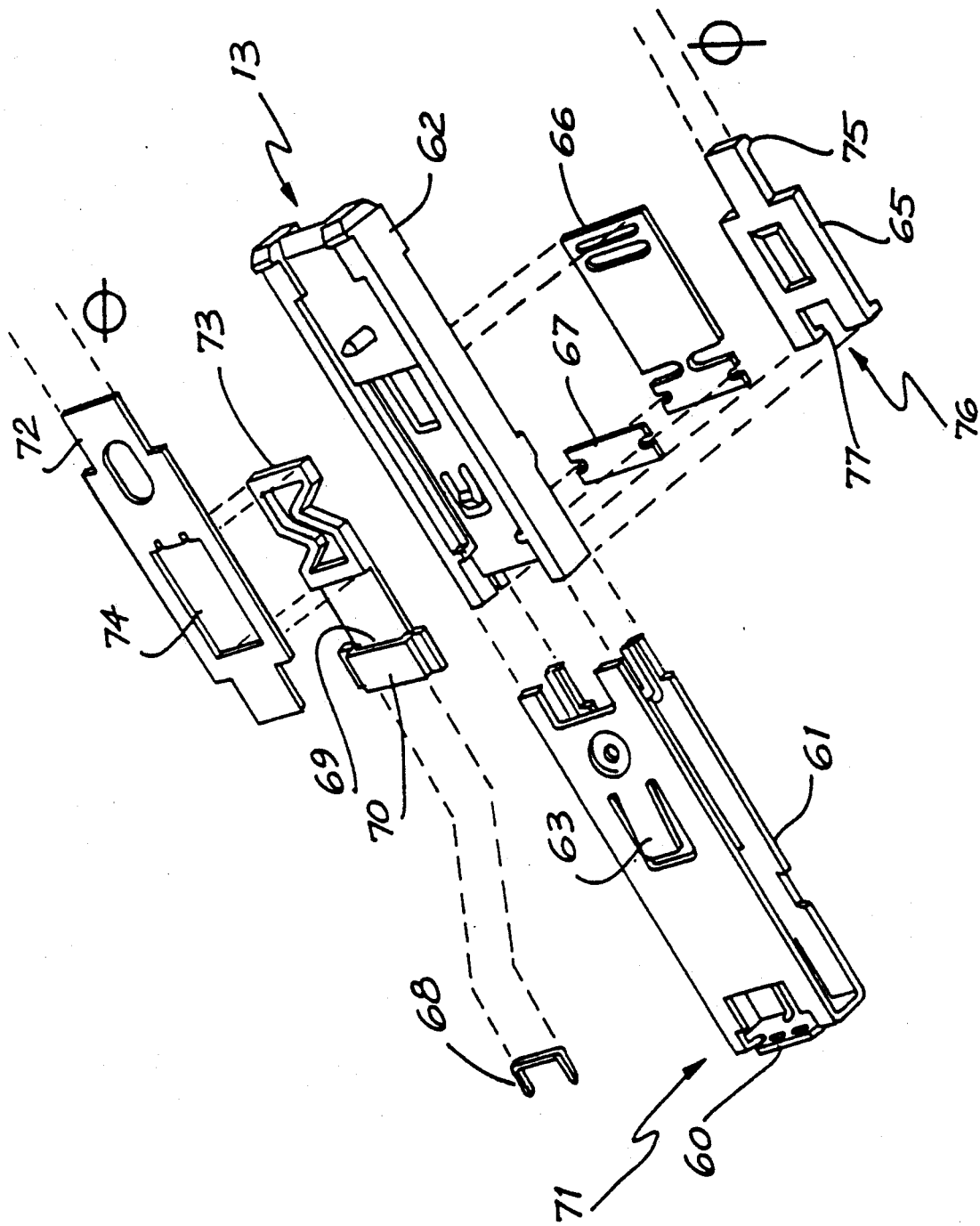
FIG. 4 is an exploded view of the cartridge shown in FIGS. 1 and 2.

The cartridge 13 shown in FIGS. 2 and 4 has an anvil 60 formed at one end of U-shaped housing 61 which receives a track portion 62. On the top face of the housing 61 there is a spring latch 63 which engages an abutment face 64 (see FIG. 5) beneath the cartridge eject button 19 when the end of the cartridge 13 is loaded into the receiving portion 12. Slidably mounted between the bottom of the housing 61 and the lower face of the track 62 is a cuff adjustment puller 65 and a carrier 66 which supports a cutting blade 67.

A staple 68 sits on a staple bed 69 beneath clamp 70 with the legs of the staple facing towards the anvil 60 but clear of cuff passageway 71. The staple 68 is moved towards the anvil 60 by a driver 72 that is connected to the driver extension 38 of the handle or body portion 11. The driver 72 extends beneath the cuff clamp 70.

The staple driver 72 is biased rearwardly by spring 73 which is located in a recess 74 in the driver 72. When the driver 72 is moved towards the anvil 60 by the driver extension 38 under the action of the toggle mechanism 34 and 38, the clamp 70 is moved to engage the overlapping portions of the cuff in the passageway 71 and the staple 68 is moved towards the anvil 60. The spring 73 takes account of the shorter distance moved by the clamp 70.

The manner of connection of the cartridge 13 to the handle or body portion 11 is shown in detail in FIGS. 5 to 7. When the cartridge 13 is inserted into the handle or body portion 11, the lug 56 of the cuff puller extension 52 is above the recess 57 in the base 24 (see FIG. 5). As the cartridge 13 is advanced, the locking lug 75 on the rear end of the puller 65 cams the lug 56 on the puller extension 52 down into the recess 57 (see FIG. 6). Upon further advancement of the cartridge 13, the locking lug 75 engages the slot 55 in the puller extension 52 (see FIG. 7) and the spring latch 63 engages the face 64 to lock the cartridge in place. As shown in FIG. 7, once the locking lug 75 is engaged in the slot 55 there is sufficient room for the lug 75 to move vertically to effect disengagement from the slot 55.

Figures 8, 9:
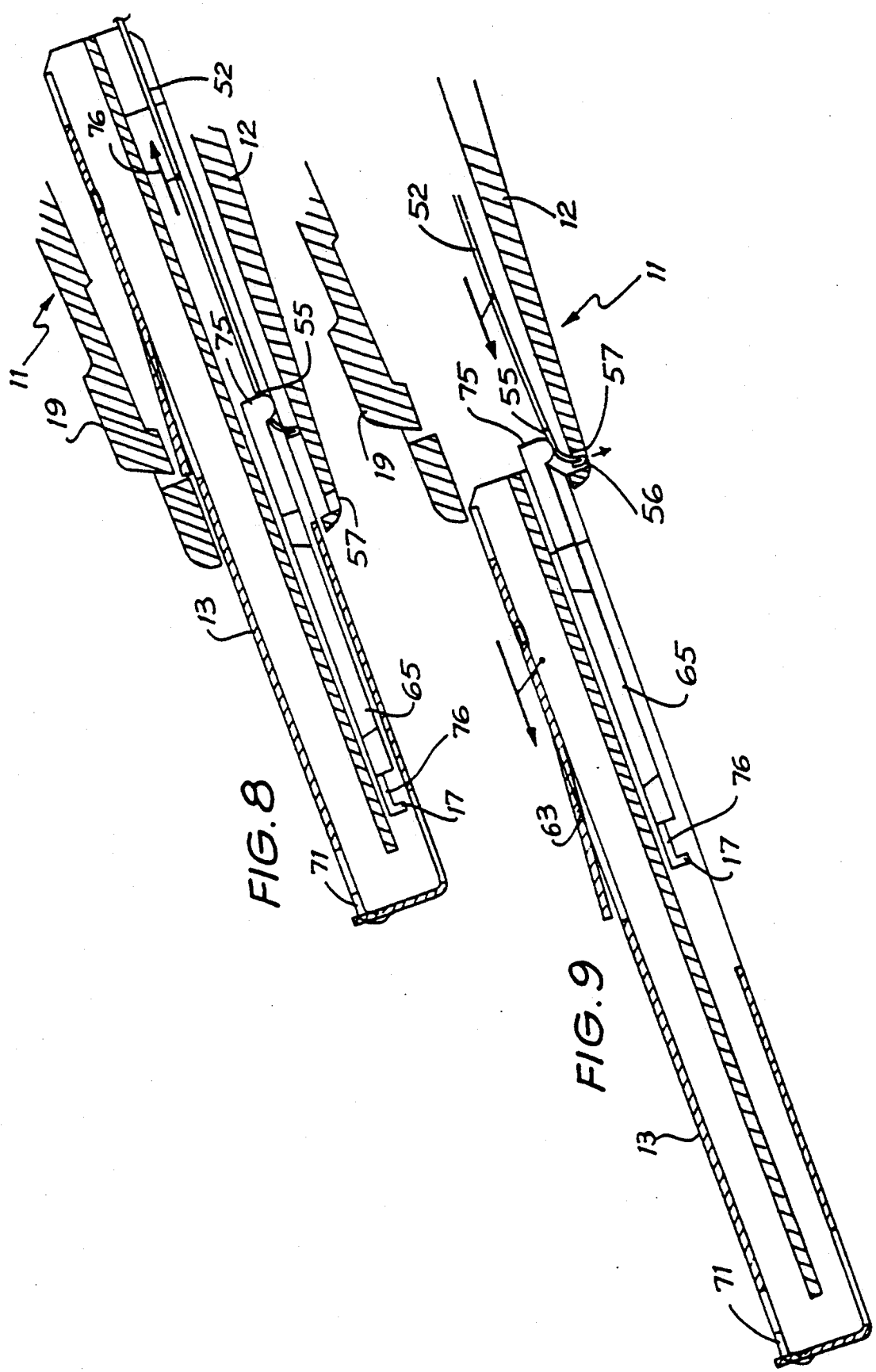
FIG. 8 is a view similar to FIG. 7 but showing movement of the puller and puller extension as a cuff is adjusted.
FIG. 9 is a view similar to FIG. 5 but showing disengagement of the puller from the puller extension.

As will be described below, the cuff 14 is tightened around the vein 15 by moving the cuff puller extension 52 in the direction of the arrow 76 in FIG. 8 which moves the lug 75 and slot 55 connection further away from the recess 57. When the cartridge 13 is removed from the body portion 11, the cuff puller extension 52 is, as shown in FIG. 9, returned to the position shown in FIG. 6 before the lug 75 can be disengaged from the slot 55 as a consequence of the lug 56 being carried down into the recess 57 in the base 24. At the same time, the thumb slide abutment 42 of the tensioner 17 is returned to load position in which transverse lug 44 engages locking recess 45.

Figure 10:
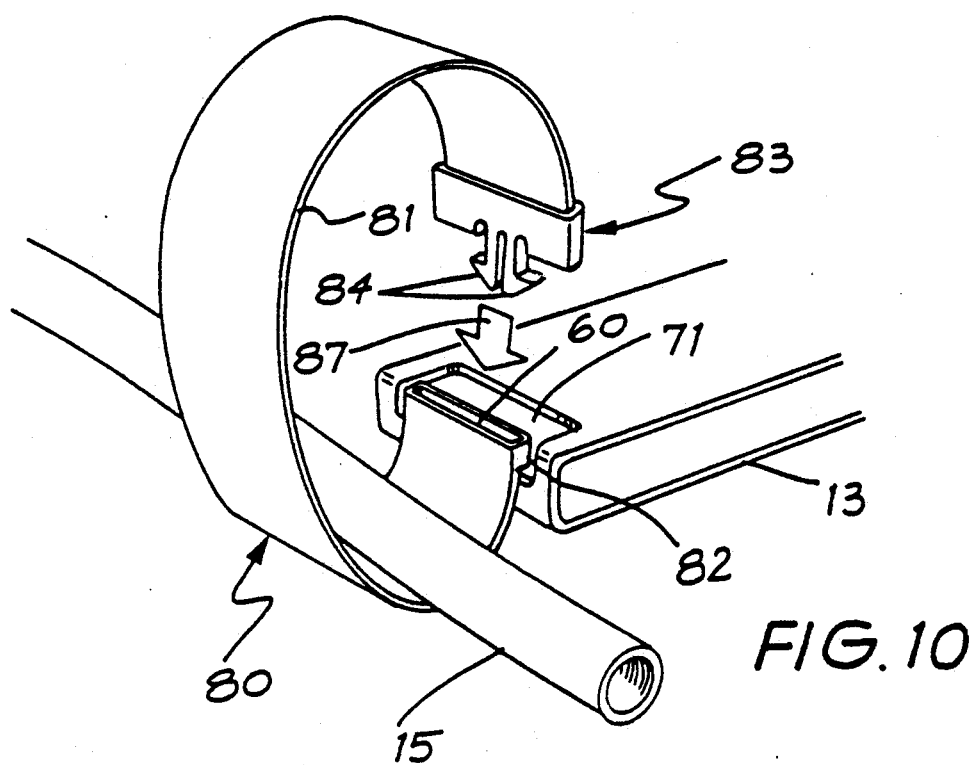
FIG. 10 is a cut-away perspective showing the coupling of a cuff leader to the applicator.
Figure 11:
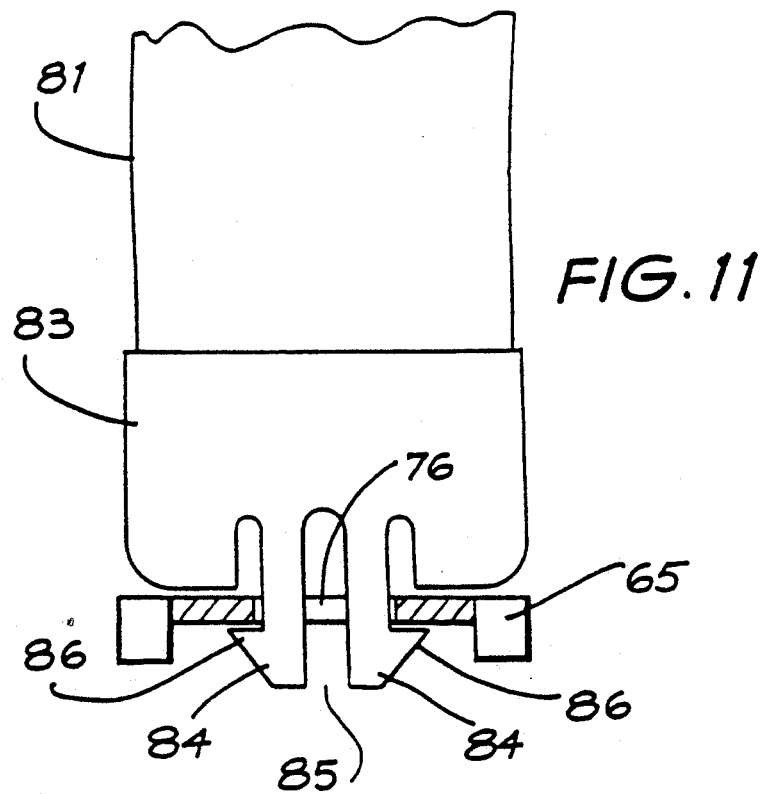
FIG. 11 is a broken away end view showing the connection between the cuff leader and the cuff puller.

The applicator shown in FIGS. 1 and 2 is particularly useful for applying the cuff 80 shown in FIG. 10 which consists of a strap portion 81 which forms a loop with a substantially smooth inner surface having a head or loop portion 82 by means of which it is attached to the top of the anvil 60. The strap portion 81 is passed around the vein 15 and the leader 83 of the cuff 80 is inserted into passageway 71 and through aperture 76 in the end of the cuff puller 65. The leader 83 has a pair of tangs 84 on either side of a head slot 85 formed in the leader and the tangs have outwardly directed barbs 86 by means of which the strap 81 is pulled by the puller 65 under the movement of the tensioner 17.

The leader 83 is inserted in the direction of arrow 87 in FIG. 10 and the tangs 84 are forced together by the contact between the side faces of the barbs 86 and the sides of the aperture 76 in the front end of cuff puller 65. After sufficient movement, the barbs 86 pass through the aperture 76 with a clip-like noise to indicate to the surgeon that the leader 83 has positively engaged the cuff puller 65.

Figure 12:
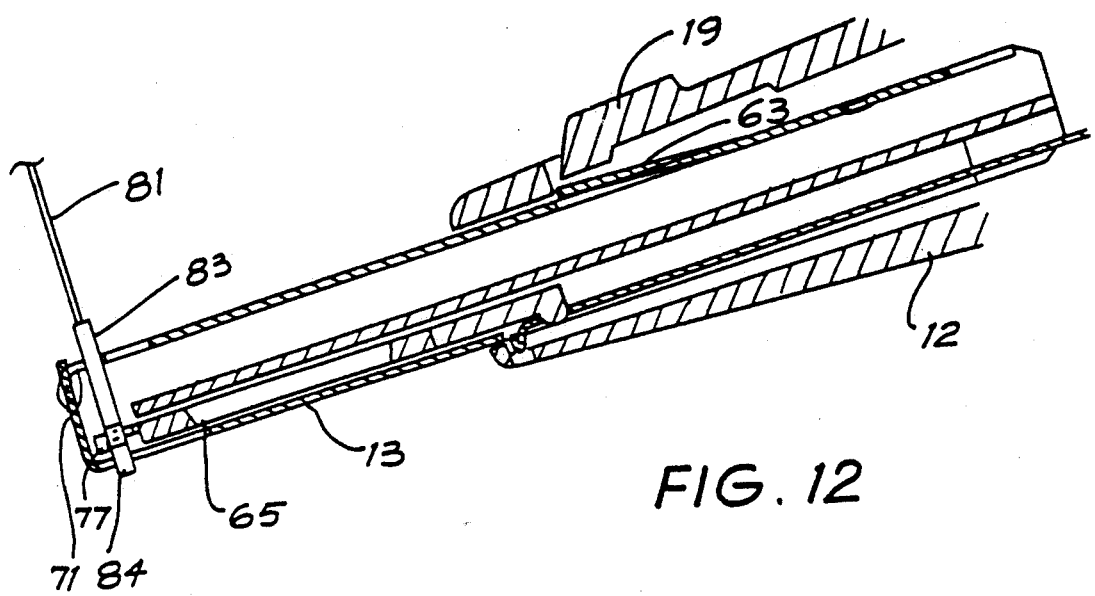
FIG. 12 is a cross-sectional view showing initial location of the cuff leader.
Figure 13:
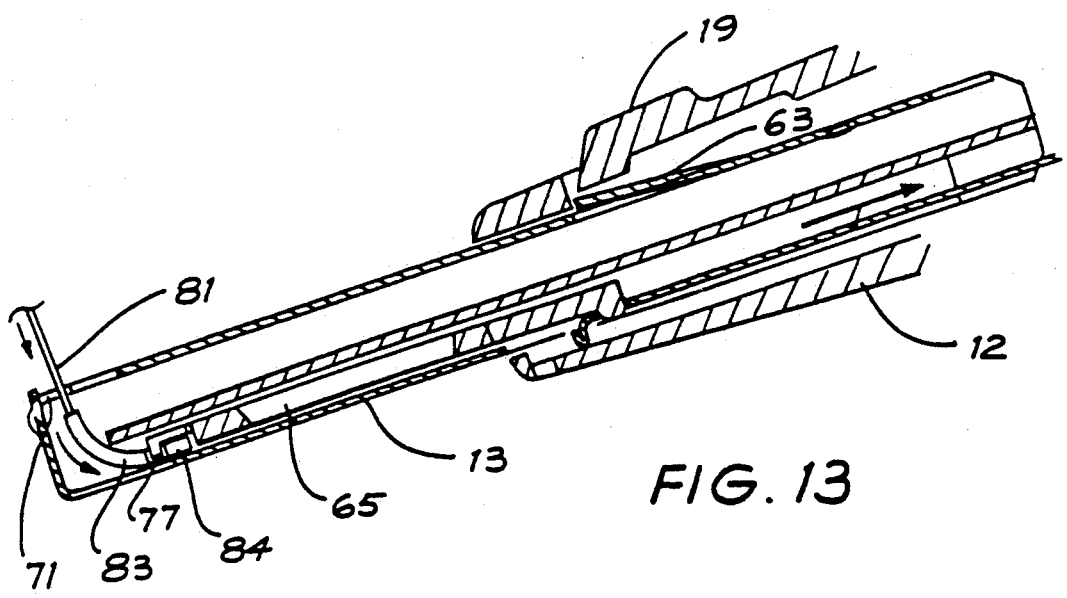
FIG. 13 is a view similar to FIG. 12 showing the cuff leader connected to the cuff puller of the cartridge.

The cuff puller 65 is then drawn to the right of FIGS. 12 and 13 by the action of the tensioner 17 so that the leader 83 of the cuff rotates over the leading edge of the track portion 62. After sufficient movement of the cuff puller 65, the leader 83 of the cuff lays parallel to the cuff puller 65 (as shown in FIG. 13) with the rear of the barbs 86 locked behind the downwardly depending flanges 77 of the puller 65.

Figure 14:
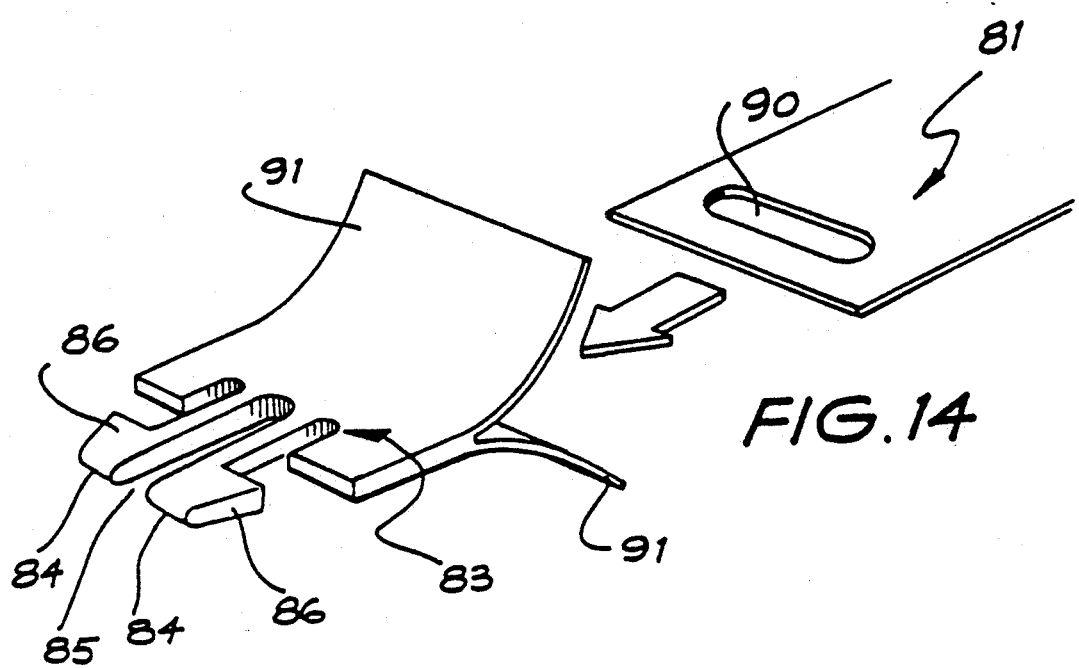
FIG. 14 is a partially cut-away perspective view of a cuff leader during assembly.
Figure 15:
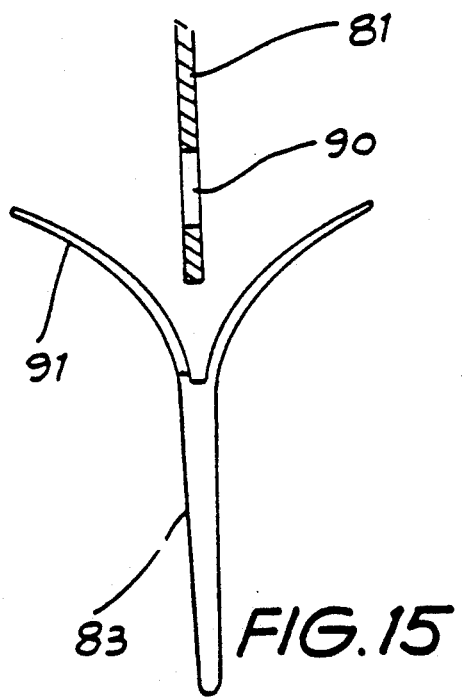
FIG. 15 is a cross-sectional view of cuff leader as shown in FIG. 14.
Figure 16:
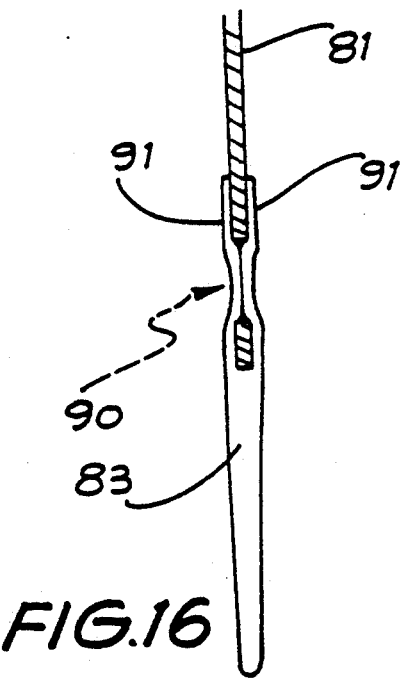
FIG. 16 is a view similar to FIG. 15 with the cuff leader secured.

Various methods of forming the leader 83 of the cuff 80 are shown in FIGS. 14 to 16, 17 to 21, 22 and 23, and 24 and 25. In the embodiment of FIGS. 14 to 16, the cuff strap 81 is die cut to provide an aperture 90. The leader 83 consists of a one piece polyethylene molding having bifurcated ends 91 which receive the end of the strap 81 (see FIGS. 14 and 15). When assembled, the ends 91 are heat sealed together with the ends 91 meeting through the aperture 90. The ends 91 may be sealed together ultrasonically in which case one of the ends 91 will be provided with a bead that is located in the aperture 90.

In the embodiments of FIGS. 17 to 21, the leader 83 which is of a slightly different configuration to that shown in FIGS. 10 to 16 is formed from folded sheet material such as polyethylene. In the FIG. 17 embodiment, the leader is preformed with the slots 85 and 85a and in the embodiment of FIGS. 18 to 21, the leader 83 and strap 81 are blanks which are die cut to size and configuration after the leader blank 83 has been sealed over the strap 81. As before, the strap has an aperture 90 through which the ends of the leader meet when the heat seal is effected. The seal areas are shown by numerals 92 and 93 in FIG. 21.

Figure 22:
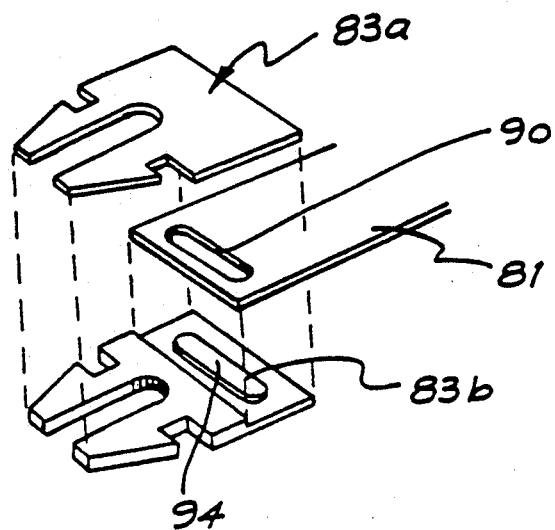
FIG. 22 is a cut-away perspective view of a modified cuff leader during assembly.
Figure 23:
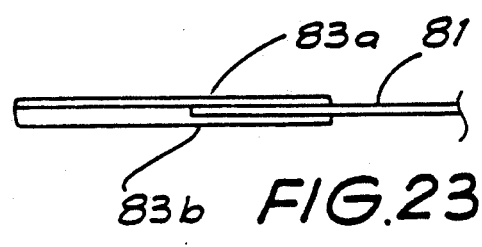
FIG. 23 is a cross-sectional view of the completed cuff leader shown in FIG. 22.

Another embodiment of the leader is shown in FIGS. 22 and 23. In this instance, the leader is formed from two pieces 83a and 83b of low density polyethylene. The lower leader piece 83b has a heat seal rib 94 dimensioned to be located in aperture 90. The mating surfaces of the leader pieces 83a and 83b are heat sealed together as shown in FIG. 23.

Figure 24:
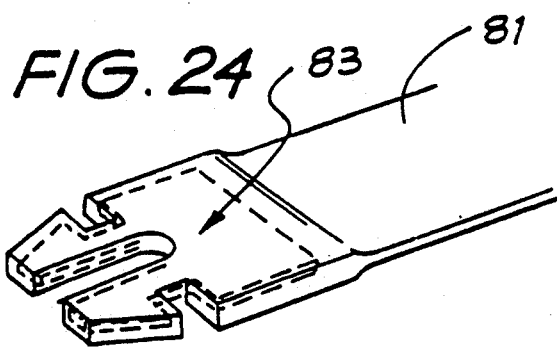
FIG. 24 is a cut-away perspective view of a modified cuff leader.
Figure 25:
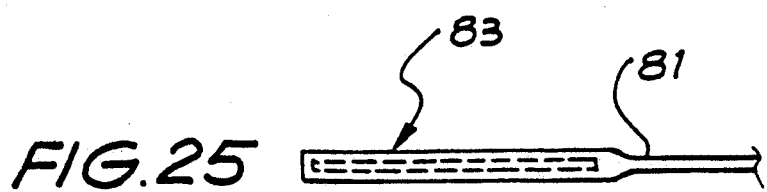
FIG. 25 is a cross-sectional view of the cuff end shown in FIG. 24.

In the embodiment of FIGS. 24 and 25, the leader 83 consists of a low density polyethylene insert molded within the silicone strap 81.

As mentioned above, the cartridge 13 contains the anvil 60, the staple 68, the staple driver 72 and the cuff puller 65. To apply a cuff, the cartridge 13 is coupled to the handle or body portion 11 and the strap 81 is then fed around the vein 15 and the leader 83 connected to the cuff puller 65. The diameter of the loop formed by the strap 81 is then varied by the tensioner 17 until valve competence is achieved.

After competence of the venous valve has been tested, the staple driver extension 38 is pushed forward by activating the side actuators or triggers 18 and as it moves towards the strap 81, the clamp 70 presses the overlying portion of the strap 81 firmly against the head or loop portion 82. The staple 68 is then forced forward by the driver 72 and passes through the strap 81 and the head or loop portion 82 to be closed by the staple anvil 60. The free end of the strap 81 beyond the staple 68 is removed by the cutting blade 67. The applicator 10 is then detached from the cuff 14 and the cuff is sutured into position to prevent the cuff from slipping along the valve segment of the vein 15.

Figure 26:
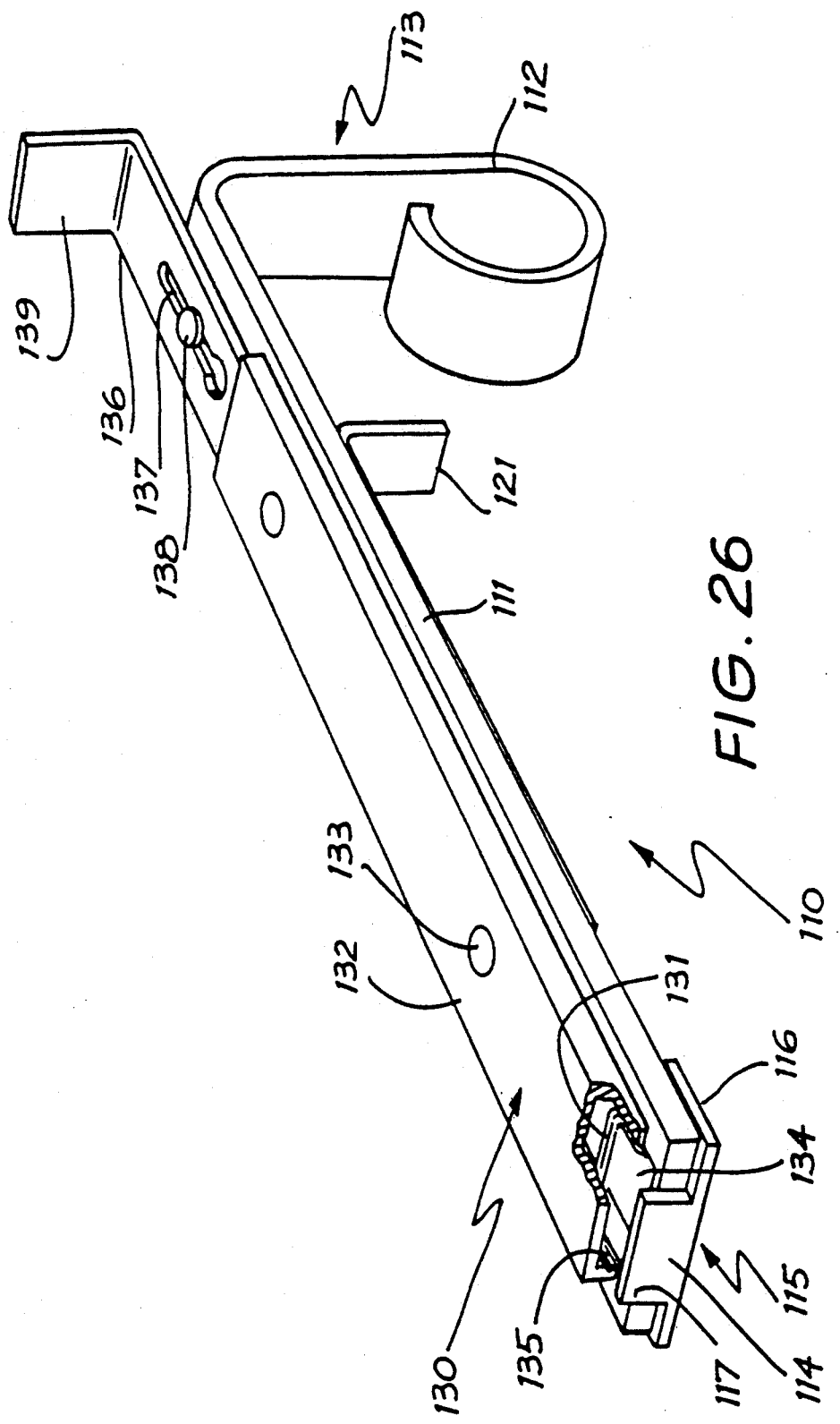
FIG. 26 is a perspective view, from above, of a venous cuff applicator according to a second embodiment of the invention.

The applicator 110 shown in FIGS. 26 and 27 includes a body portion 111 having a handle 112 at one end 113 and a cuff holder 114 at the other end 115. The applicator 110 is suitable for applying a venous cuff of the kind shown in FIG. 29 which consists of an elongated strap 140 having a free end 141 and a loop 142 at its other end 143. The loop 142 extends above the upper face 144 of the strap 140.

At the loop end 143 of the strap 140 there is a transverse tag 145 that carries opposed securing ears 146 by means of which the cuff is sutured to surrounding tissue or to the vein. A cut-out 147 is provided in the free end 141 of the strap 140 to permit attachment of the free end of the strap to the applicator shown in FIGS. 26 and 27.

Figure 29:
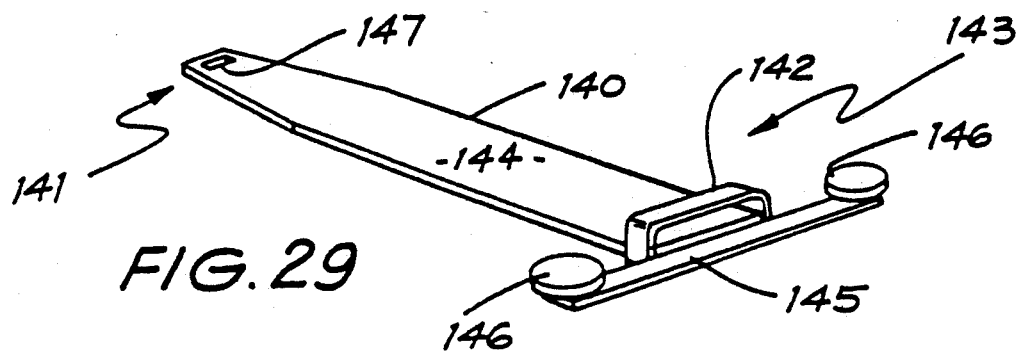
FIG. 29 is a perspective view of a cuff to be applied by the applicator shown in FIGS. 26 and 27.

The cuff holder 114 shown in FIG. 26 consists of a base portion 116 secured to the bottom face of the body portion 111 and an upstanding tab or pillar 117 which receives the loop 142 of the strap 140 as shown in FIG. 29. A modification of the holder 114 is shown in FIG.

27 where it is integral with the body portion 111 and thus does not have a base portion 116.

Adjacent to the cuff holder 114 there is an aperture 118 (see FIG. 27) through which the free end 141 of the strap 140 passes after the strap has been encircled around a vein.

A cuff adjustor 120 slidably mounted on the bottom face of the body portion 111 has a finger grip portion 121 adjacent the handle 112 of the applicator 110 and attachment means 122 at its other end adapted to engage the cut-out 147 in the strap 140 as is shown in FIG. 28. The cuff adjustor 120 is friction mounted with respect to the applicator body portion. In this embodiment of the invention, friction is achieved with a ratchet mechanism which allows the adjustor 120 to be moved relative to the handle 112 and to be kept in any selected position. If desired, the ratchet can have increments of 3.14 mm so that movement of the adjustor 120 by one ratchet tooth would result in a 1 mm change in the diameter of the cuff.

In this instance, the means for securing the overlapping portions of the strap 140 includes a stapling gun 130 slidably mounted on the upper face of the body 111 which has a body portion 132 that is slidably attached to the body portion 111 of the applicator 110 by studs 133. At the end of the stapling gun body 132, adjacent to the pillar 117, there is a recess 134 adapted to receive a staple 131 inserted through the opening 135 at the end of the stapling gun body 132. The end of the stapling gun body 132 is clear of the aperture 118 so as to prevent fouling of the cuff. Although not shown in the drawings, the pillar 117 of the cuff holder 114 has grooves on its inwardly directed face 119 (see FIG. 30) so that the pillar 117 acts as an anvil for closing the staple 131.

Slidably mounted on the upper face of the body portion 111 of the applicator 110 is an operating lever 136 for the stapling gun 130. The lever 136 has a keyway 137 through which passes a fastener 138. The lever 136 projects beyond the handle 112 of the applicator 110 and has an upstanding tab 139 operable by the thumb of the surgeon's hand while gripping the handle 112.

Both the stapling gun 130 and the operating lever 136 automatically move and remain in a retracted position so that the aperture 118 (FIG. 27) in the cuff holder 114 is always open and the staple 131 remains in the recess 134 until the operating lever 136 is actuated.

Figure 30:
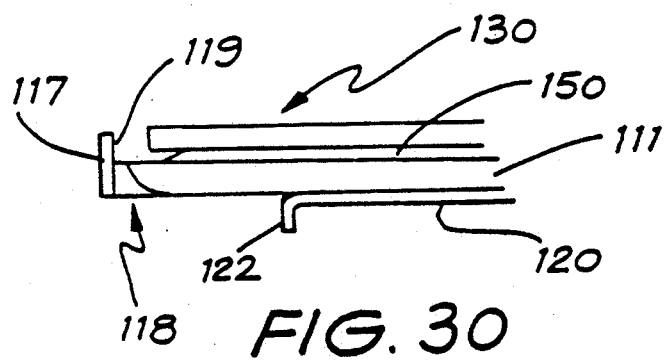
FIG. 30 is a view similar to FIG. 28 showing a modification of the applicator shown in FIGS. 26 and 27, and, FIG. 31 is a further modification of the applicator shown in FIGS. 26 and 27.

In the modification of the invention shown in FIG. 30, a guillotine 150 is located above the body portion 111 of the applicator and beneath the stapling gun 130 to trim excess strap from the cuff. The activation of the guillotine 150 can be separate to or in conjunction with the stapling action.

Figure 31:
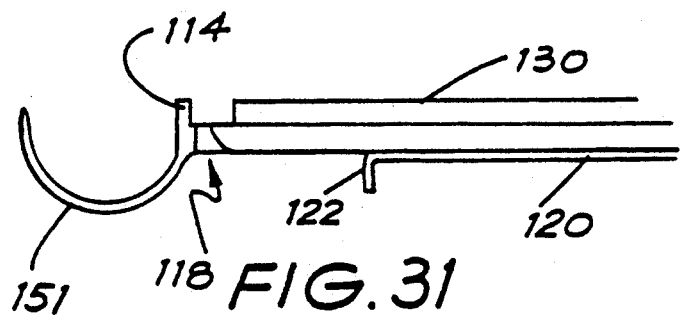

In the modification of the invention shown in FIG. 31, a guide 151 is integral with the holder 114 to assist in the formation of the loop of the strap around the vein. The guide need not be integral with the holder. Automatic feeding of the strap may be incorporated into the applicator.

The applicator may be designed as a disposable implement or for multiple use. In the latter case, both the stapling gun and the cuff adjustor are easily detachable from the body of the applicator for safe sterilization and for convenient loading of the staple gun. As will be apparent from FIG. 28, the cuff is attached to the applicator by slipping the loop 142 over the pillar 117. The strap 140 is then fed around the vein by either curved forceps or by the guiding action of the guide 151. The free end 141 of the strap 140 is inserted through the aperture 118 so that the strap is located close to or overlies the loop 142. The cut-out 147 in the free end of the cuff is attached to the hook 122 of the cuff adjustor 120.

The feeding of the strap around the vein, the insertion of the free end of the strap through aperture 118 and the attachment of the free end of the strap to cuff adjustor 120 may be carried out automatically.

The diameter of the loop formed by the strap is then varied by moving the cuff adjustor 120 until valve competence is achieved.

After competence of the valve has been tested, the stapling gun 130 is activated and as it moves towards the strap 140, the gun body 132 presses the strap firmly against the loop 142. The staple 131 is then forced forward by the operating lever 136 and passes through the strap 140 and the loop 142 to be closed by the anvil in the pillar 117. In the embodiment of the invention shown in FIG. 30, the free end of the strap beyond the staple can be removed by the guillotine 150. The cuff is then detached from the applicator and sutured into position to prevent the cuff from slipping off the valve segment of the vein.

As will be apparent from the above description, the applicators of the invention allow a single surgeon to apply a cuff to a vein. With one hand, the surgeon using the applicator can adjust the cuff to the desired diameter and then test the valve for competence. After final adjustment of the diameter, the surgeon then staples the overlapping portions of the strap together. If need be, the free end of the strap is trimmed and the cuff removed from the applicator.

The applicator described above allows the surgeon to make fine adjustments to the diameter of the cuff. This is important as studies have shown that there is a certain diameter at which a venous valve achieves optimal competence. Any reduction below this diameter results in unnecessary obstruction of the vein which can cause an exacerbation of the venous disease.

The cuff as described above for use with the applicators of the invention is made from biocompatible, implantable material that is not stretchable as blood flow pressure such as cured silicon rubber sheeting reinforced with a woven polyester.

Various modifications may be made in details of design and construction of the applicator without departing from the scope and ambit of the invention.

We claim:

1. An applicator for applying an elongated strap around an object, which comprises:
   a strap;
   means for anchoring one end of the strap,
   means movable with respect to the anchoring means for engaging the other end of the strap after the strap has been formed into a loop around the object and positioned over the anchored end, said movable means including means for moving said other end of the strap so as to tighten and loosen the perimeter of the loop, and
   stapler means external of said loop and mounted within the applicator for securing the overlapping portions of the strap.

2. An applicator according to claim 1, which comprises a staple positioned in the applicator wherein the means for anchoring one end of the strap comprises a pillar that acts as an anvil for closing the staple.

3. An applicator according to claim 1, wherein said strap includes a leader and the means for engaging the other end of the strap, is a strap puller having means for engaging said leader on said other end of the strap.

4. An applicator according to claim 3 wherein the strap puller has an opening which receives a pair of spaced apart tangs on the leader as said tangs are forced together.

5. An applicator according to claim 4 wherein the strap puller has flanges adjacent the opening against which barbs on the tangs bear to lock the said other end of the strap to the strap puller.

6. An applicator according to claim 3 wherein the strap puller has a lug adapted to engage an aperture in the said other end of the strap.

7. An applicator according to claim 1 and further including means for trimming off any excess of the strap once the overlapping portions have been secured together.

8. An applicator for applying an elongated strap formed into a loop with a substantially smooth inner surface around an object, comprising:

a staple cartridge and a handle portion, said staple cartridge including a staple, an anvil and a staple driver for moving the staple towards the anvil, said cartridge further including means external of said loop for anchoring one end of the strap and a strap puller for engaging the other end of the strap after said strap has been formed into said loop around the object and overlies the anchored end, said handle portion including tensioning means for being connected to the strap puller to tighten and loosen the loop, trigger means for actuating the staple driver and means for connecting the cartridge to the handle portion.

9. An applicator for securing an elongated strap around an object with one end of the strap being anchored and the other end overlying said one end after said other end has been looped around the object, said applicator comprising a body portion, a strap adjuster within the body portion having adjustment means projecting from the body portion for tightening and loosening said strap, stapler means located external of said loop and mounted within the applicator and trigger means within the body portion having actuating means projecting from the body portion for activating the stapler means for securing overlying portions of the strap together.

10. An applicator according to claim 9 wherein the strap adjuster includes a toothed rank engageable with a stop to permit incremental movement of the tensioner.

11. A cartridge for use in securing an elongated strap shaped as a loop with a substantially smooth inner surface around an object with one end of the strap overlying the other end of the strap after the one end has been looped around the object, said cartridge comprising anchor means for receiving said other end of the strap, and means for engaging an external portion of the one end of the strap after the strap has been formed as a loop, said engaging means being movable so as to tighten and loosen the perimeter of the loop and including staple drive means for driving a staple through the overlying portions of the strap.

12. A cartridge according to claim 10 and including an anvil for closing the staple.

13. A cartridge according to claim 12 and including a staple.

* * * * *

UNITED STATES PATENT AND TRADEMARK OFFICE
CERTIFICATE OF CORRECTION

PATENT NO.  :  5,211,649
DATED       :  May 18, 1993
INVENTOR(S) :  Wolfgang W. Kohler et al.

It is certified that error appears in the above-indentified patent and that said Letters Patent is hereby corrected as shown below:

On the title page, Item [63],

The Related Application Data has been omitted, should read:

--Continuation Application of PCT/AU88/00036 filed Feb. 10, 1988, now abandoned.--

Signed and Sealed this

First Day of February, 1994

Attest:

BRUCE LEHMAN

*Attesting Officer*        *Commissioner of Patents and Trademarks*